US00PP20403P2

(12) United States Plant Patent
Van Zanten

(10) Patent No.: US PP20,403 P2
(45) Date of Patent: Oct. 6, 2009

(54) ***CHRYSANTHEMUM* PLANT NAMED 'GG GOLA 08'**

(50) Latin Name: *Chrysanthemum morifolium*
Varietal Denomination: GG GOLA 08

(75) Inventor: Leo Van Zanten, Oxnard, CA (US)

(73) Assignee: GroLink Plant Company, Oxnard, CA (US)

( * ) Notice: Subject to any disclaimer, the term of this patent is extended or adjusted under 35 U.S.C. 154(b) by 0 days.

(21) Appl. No.: 12/218,788

(22) Filed: Jul. 18, 2008

(51) Int. Cl.
*A01H 5/00* (2006.01)

(52) U.S. Cl. ..... Plt./286

(58) Field of Classification Search ..... Plt./286, Plt./297

See application file for complete search history.

*Primary Examiner*—June Hwu
(74) *Attorney, Agent, or Firm*—Mark P. Bourgeois

(57) ABSTRACT

A new and distinct *Chrysanthemum* plant cultivar is disclosed, characterized by large anemone type inflorescences, consistent flowering response to short days, blooming consistently after 53 days of short day length, lavender ray florets and large pale yellow discs, and a free branching habit.

1 Drawing Sheet

Latin name of the genus and species: *Chrysanthemum morifolium.*

Variety denomination: 'GG GOLA 08'.

BACKGROUND OF THE INVENTION

The new cultivar 'GG GOLA 08' is a product of a cross between the male parent 'Summer Time' (not patented in the United States) and the female parent 'PLT0901' (unpatented). The new cultivar was discovered and selected by Leo Van Zanten in April of 2003 in Oxnard, Calif.

Asexual reproduction of the new cultivar 'GG GOLA 08' by terminal cuttings was performed in Oxnard, Calif., and has shown that the unique features of this new cultivar are stable and reproduced true to type on successive generations.

SUMMARY OF THE INVENTION

The cultivar 'GG GOLA 08' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG GOLA 08.' These characteristics in combination distinguish 'GG GOLA 08' as a new and distinct *Chrysanthemum* cultivar:

1. Large, lavender, anemone-type inflorescences;
2. Pale yellow discs;
3. Free branching habit; and
4. Consistent flowering response to short days, blooming consistently after 53 of short day length.

Plants of the new cultivar 'GG GOLA 08' are similar to plants of the male parent variety, 'Summer Time' in most horticultural characteristics, however plants of the new cultivar 'GG GOLA 08' are shorter. Also, the new cultivar 'GG GOLA 08' has a smaller inflorescence diameter and longer inflorescence longevity. Additionally, the ray florets of 'GG GOLA 08' are pink compared to the yellow ray florets of the male parent. Finally, the inflorescence form of 'GG GOLA 08' is anemone compared to the daisy type inflorescence form of the male parent.

Plants of the new cultivar 'GG GOLA 08' are similar to plants of the female parent variety, 'PLT0901' in most horticultural characteristics, however plants of the new cultivar 'GG GOLA 08' are shorter but have a wider plant spread. Also, the new cultivar 'GG GOLA 08' has a smaller inflorescence diameter. Additionally, the ray florets of 'GG GOLA 08' are longer and a lighter pink than the lavender florets of the female parent. Finally, 'GG GOLA 08' has a shorter response time.

In comparison to the commercially available variety 'GG GOFRT 05' (U.S. Plant Pat. No. 18,379), 'GG GOLA 08' has a smaller plant height and has anemone-type inflorescences compared to the daisy-type inflorescence of 'GG GOFRT 05'. Additionally, the new variety 'GG GOLA 08' has a larger inflorescence diameter and lavender ray florets compared to the dark pink ray florets of the comparable variety. Finally, 'GG GOLA 08' has a pale yellow disc compared to the green disc of 'GG GOFRT 05'.

BRIEF DESCRIPTION OF THE PHOTOGRAPH

The accompanying photograph illustrates in full color a typical plant of 'GG GOLA 08' grown in a 6 inch container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GG GOLA 08' plants grown in Oxnard, Ventura County, Calif., during the months of May through October 2006. The growing temperature ranged from 12° C. to 15° C. at night to 12°

C. to 20° C. during the day. Measurements and numerical values represent averages of typical flowering types.
Botanical classification: *Chrysanthemum morifolium* 'GG GOLA 08.'
Commercial classification: Pot-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 14 cm.
Plant spread: Approximately 30 cm.
Growth rate: Moderate.
Branching characteristics: Free branching.
Length of lateral branches: Approximately 9 cm.
Number of leaves per lateral branch: Approximately 28.
Age of plant described: Approximately 102 days.

FOLIAGE

Leaf:
*Arrangement.*—Alternate single.
*Average length.*—Approximately 5 cm.
*Average width.*—Approximately 2.9 cm.
*Shape of blade.*—Ovate.
*Apex.*—Acuminate.
*Base.*—Attenuate.
*Attachment.*—Stalked.
*Margin.*—Palmately lobed, sinuses between lateral lobes parallel to divergent.
*Texture of top surface.*—Lightly pubescent.
*Texture of bottom surface.*—Lightly pubescent.
*Leaf internode length.*—Approximately 1.2 cm.
*Color.*—Young foliage upper side: Near Green 137A. Young foliage under side: Near Green 137C. Mature foliage upper side: Near Green 137A. Mature foliage under side: Near Green 137D.
*Venation.*—Type: Palmately net. Venation color upper side: Near Green 137A. Venation color under side: Near Green 137B.
Petiole:
*Average length.*—Approximately 1.5 cm.
*Color.*—Near Green 137A.
*Diameter.*—Approximately 0.3 cm.

BLOOM

Inflorescence:
*Flowering habit.*—Induced by darkness period greater than 13.5 hours, approximately 49 days of appropriate day length required to induce and develop blooms.
*Inflorescence form.*—Anemone.
*Number of inflorescences per lateral branch.*—Approximately 16.
*Inflorescence diameter.*—Approximately 6.2 cm.
*Inflorescence depth.*—Approximately 1.5 cm.
*Inflorescence disc diameter.*—Approximately 2.2 cm.
*Inflorescence longevity on plant.*—Approximately 35 to 42 days.
*Persistence.*—Persistent.
*Fragrance.*—None detected.

Ray florets:
*Appearance.*—Matte.
*Texture.*—Smooth.
*Average number of ray florets per inflorescence.*—22.
*Average number of whorls.*—2.
*Shape.*—Oblanceolate.
*Aspect.*—Flat.
*Margin.*—Entire.
*Apex.*—Obtuse.
*Length.*—Approximately 2.9 cm.
*Width.*—Approximately 1 cm.
*Color.*—Upper surface at first opening: Between Purple 75C and 75D. Upper surface at maturity: Near Purple 75C with striations of near Purple 75A and 75B. Upper surface at fading: Near Purple 75D. Under surface at first opening: Near Purple 75C. Under surface at maturity: Near Purple 75D. Under surface at fading: Near Purple 75D.
Disc florets:
*Appearance.*—Shiny.
*Texture.*—Smooth.
*Average number of florets per disc.*—Approximately 241.
*Shape.*—Cylindric.
*Apex.*—Obtuse.
*Average length.*—Approximately 0.7 cm.
*Average width.*—Approximately 0.2 cm.
*Color.*—At first opening: Near Green-Yellow 1B. At maturity: Near Yellow 2D at edges, closer to Yellow 4A at center. At fading: Near Yellow 2D.
Peduncle:
*Length.*—At terminal end (shortest): Approximately 2.3 cm. At lateral end (longest): Approximately 4.5 cm.
*Angle to stem.*—Acute.
*Strength.*—Moderate.
*Color.*—Near Green 137D.
*Habit.*—Upright.
*Diameter.*—Approximately 0.3 cm.
*Surface texture.*—Lightly pubescent.
Inflorescence bud:
*Length.*—Approximately 1.4 cm.
*Diameter.*—Approximately 1.2 cm.
*Form.*—Globular.
*Color.*—Near Purple 75D.
Involucral bracts (phyllaries):
*Appearance.*—Matte.
*Texture.*—Lightly pubescent.
*Number.*—Approximately 25.
*Shape.*—Lanceolate.
*Margin.*—Entire.
*Apex.*—Obtuse.
*Length.*—Approximately 0.4 cm.
*Width.*—Approximately 0.3 cm.
*Color.*—Upper side: Near Green 137A. Under side: Near Green 137A.

REPRODUCTIVE ORGANS

Ray florets:
*Number of pistils per floret.*—1.
*Stigma shape.*—2 branched.
*Stigma color.*—Near Yellow 5A.
*Style color.*—Near Yellow-Green 154D.
*Style length.*—Approximately 0.3 cm.
*Stamens.*—Absent.

Disc florets:

*Number of pistils per floret.*—1.
*Stigma shape.*—Cylindric.
*Stigma color.*—Near Yellow 2D.
*Style length.*—Approximately 0.1 cm.
*Style color.*—Near Green-Yellow 1D.
*Number of stamens per floret.*—Approximately 5.
*Anther shape.*—Tubular.
*Anther color.*—Near Yellow 2D.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'GG GOLA 08' as herein illustrated and described.

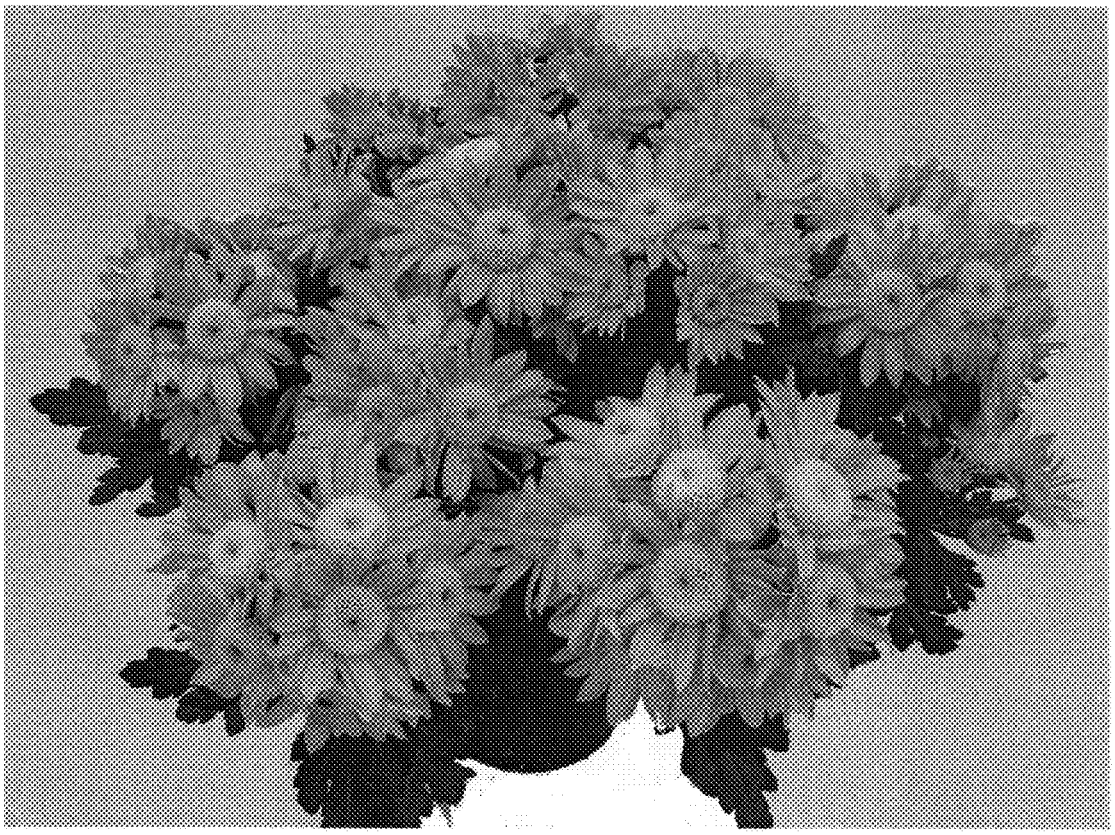

* * * * *